United States Patent [19]

Pawson

[11] Patent Number: 4,476,056

[45] Date of Patent: Oct. 9, 1984

[54] TRIFLUOROMETHOXY ANALOGS OF AROMATIC RETINOIDS

[75] Inventor: Beverly A. Pawson, Verona, N.J.

[73] Assignee: Hoffmann-La Roche Inc., Nutley, N.J.

[21] Appl. No.: 439,516

[22] Filed: Nov. 5, 1982

[51] Int. Cl.³ .......................... C09F 5/00; C09F 7/00; C11C 3/00; C07C 33/18

[52] U.S. Cl. .................................... 260/404; 260/408; 260/413; 568/437; 568/715

[58] Field of Search ................... 260/404, 408, 413 L, 260/413 K; 568/437, 715

[56] References Cited

U.S. PATENT DOCUMENTS

| | | | |
|---|---|---|---|
| 3,706,773 | 12/1972 | Anello et al. | 260/404 X |
| 3,754,009 | 8/1973 | Anello et al. | 260/408 |
| 3,984,440 | 10/1976 | Bollag et al. | 260/413 L |
| 4,054,589 | 10/1977 | Bollag et al. | 568/715 X |
| 4,137,246 | 1/1979 | Chan et al. | 260/408 |
| 4,156,016 | 5/1979 | Dalton et al. | 260/326.13 C |
| 4,163,103 | 7/1979 | Bollag et al. | 568/715 X |
| 4,171,318 | 10/1979 | Chan et al. | 260/404 |
| 4,225,527 | 9/1980 | Bollag et al. | 568/437 X |

OTHER PUBLICATIONS

Chemical Abstracts, 90:71919a, 91:117154y, (1979), 93:220789z, (1980).
Sackheim et al., Chemistry for the Health Sciences, MacMillan Co., 2nd Edit., (1973), p. 220.
Turk et al., Introduction to Chemistry, Academic Press Inc., p. 449, (1968).

*Primary Examiner*—Helen M. S. Sneed
*Attorney, Agent, or Firm*—Jon S. Saxe; Bernard S. Leon; George W. Johnston

[57] ABSTRACT

Aromatic retinoids bearing a trifluoromethoxy substituent on the aromatic nucleus which are useful as antitumor agents and in the treatment of dermatological disorders as well as a method for their manufacture are disclosed.

19 Claims, No Drawings

TRIFLUOROMETHOXY ANALOGS OF AROMATIC RETINOIDS

BACKGROUND OF THE INVENTION

The invention relates to retinoids and in particular to trifluoromethoxy analogs of aromatic substituted polyenes.

SUMMARY

The present invention concerns compounds of the formula:

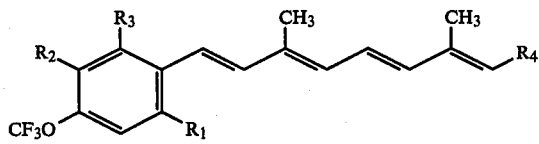

wherein $R_1$ is lower alkyl or halo; $R_2$ is lower alkyl; $R_3$ is lower alkyl or halo; $R_4$ is —CH$_2$OH,

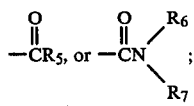

$R_5$ is hydrogen, hydroxy or lower alkoxy and $R_6$ and $R_7$ each are hydrogen or lower alkyl, or pharmaceutically acceptable salts thereof.

The compounds of formula I are useful as antitumor agents and for treating acne, psoriasis and other related dermatological disorders.

The compounds of formula I are manufactured in accordance with the reaction sequence noted in Scheme 1 described hereinafter.

DETAILED DESCRIPTION OF THE INVENTION

The present invention concerns polyene compounds, a process for their manufacture and pharmaceutical preparations containing same.

The polyene compounds included within the present invention have the formula:

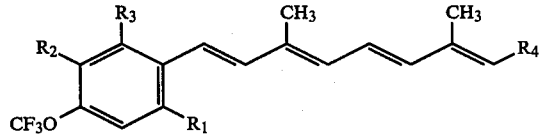

wherein $R_1$ is lower alkyl or halo; $R_2$ is lower alkyl; $R_3$ is lower alkyl or halo; $R_4$ is —CH$_2$OH,

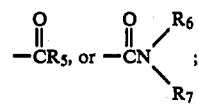

$R_5$ is hydrogen, hydroxy or lower alkoxy and $R_6$ and $R_7$ each are hydrogen or lower alkyl, or pharmaceutically acceptable salts thereof.

As used herein, lower alkyl means straight or branched chain alkyl groups having from 1 to 7 carbon atoms, (e.g., methyl, ethyl, n-propyl and isopropyl). Lower alkoxy means straight or branched chain alkoxy groups having from 1 to 7 carbon atoms (e.g., methoxy, ethoxy and isopropoxy). Aryl denotes mononuclear and polynuclear aromatic hydrocarbon groups which can be unsubstituted or substituted in one or more positions with halogen, nitro, lower alkyl or lower alkoxy. Typical aryl groups include phenyl, benzyl, napthyl, anthranyl, phenanthranyl, azulyl and the like which can be unsubstituted or substituted with one or more of the aforementioned substituents.

Halogen (halo, halide) denotes chlorine, bromine and iodine. Alkali metals include lithium, sodium, potassium and rubidium. Alkaline earth metals include beryllium, magnesium, calcium and strontium. A pharmaceutically acceptable salt means any conventional pharmaceutically acceptable salt. Among the preferred salts are alkali metal, alkaline earth metal and substituted or unsubstituted ammonium salts. An anion of an organic acid means an anion of an organic compound bearing an acidic group such as carboxyl, sulphonic, hydroxamic or sulphamic. A preferred anion is the tosyloxy ion.

Unless otherwise indicated, all formulas include cis-/trans mixtures as well as the corresponding cis and trans compounds.

All trans compounds of formula I are preferred.

In accordance with the present invention, the compounds of formula I can be prepared from a compound of the formula

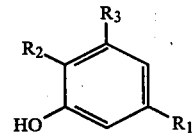

via following Scheme I:

Scheme 1

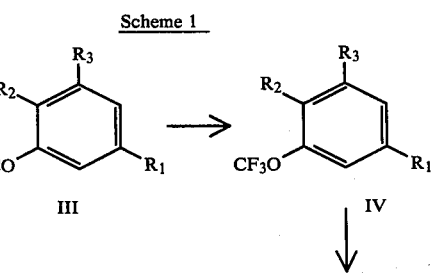

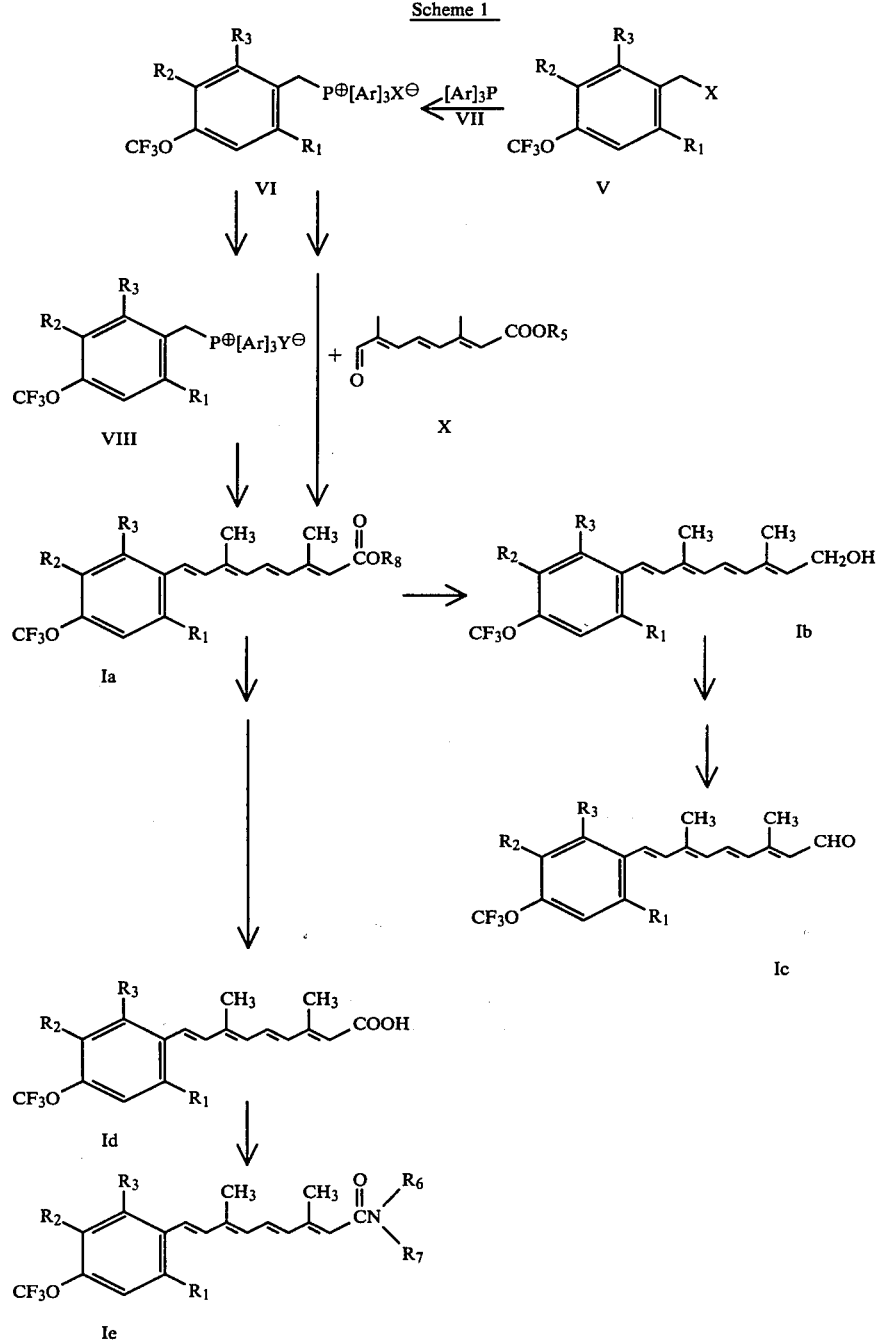

Scheme 1 wherein $R_1$ is lower alkyl or halo; $R_2$ is lower alkyl; $R_3$ is lower alkyl or halo; $R_4$ is —$CH_2OH$,

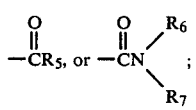

$R_5$ is hydrogen, hydroxy or lower alkoxy, $R_6$ and $R_7$ each are hydrogen or lower alkyl; $R_8$ is lower alkyl; X is halo; Ar is aryl; and Y is an anion of an organic acid.

In accordance with Scheme I, a compound of formula II is converted to a compound of formula III by any conventional derivatization of a phenol to produce a chlorothionocarbonate. A suitable method includes reacting compound II in a base such as sodium hydroxide and a nonaqueous polar organic solvent such as carbon tetrachloride or chloroform. Although temperature is not critical, the reaction generally proceeds between about −20° C. and about +20° C., preferably at about −10° C.

Compound III is then converted to compound IV by reaction with molybdenum hexafluoride according to the process of Mathey-Bensoam. More particularly, compound III is reacted with molybdenum hexafluoride in a polar organic solvent. Preferably, chlorinated solvents such as methylene chloride are utilized in the reaction. Although temperature is not critical, the reaction generally proceeds between about −50° C. and about 0° C., preferably at about −25° C.

Compound IV then is converted to compound V via any conventional halo methylation technique. Illustratively, compound IV is reacted with halomethyl methyl ether, preferably chloromethyl methyl ether in a mixture of acetic acid, hydrochloric acid, aqueous formaldehyde to form compound V. Although temperature is not critical, the reaction generally proceeds between about 50° C. and about 100° C., preferably at about 85° C.

Compound V is converted to compound VI by any conventional method for producing a substituted phosphonium salt. Illustratively, compound V is reacted via a Wittig reaction with triarylphosphine of formula VII to yield compound VI. Typical triarylphosphines include triphenylphosphine and tritolylphosphine. In a preferred compound of formula VI, Ar is phenyl and X is chloride. Although not necessary, the Wittig reaction preferably occurs in a solvent such as a polar organic solvent (e.g., toluene, ethyl acetate, and especially acetonitrile). In forming the Wittig reagent, temperature is not critical and can range from about 50° C. to about 100° C. The preferred temperature for the reaction is about 80° C.

If desirable, compound VI can be transformed to a compound of formula VIII wherein Y is an anion of an organic acid by any conventional means to exchange a halide for an organic anion. For example, compound VI can be treated with silver tosylate to yield a silver halide and compound VIII wherein Y is the tosyloxy ion.

The compounds of formulas VI and VIII can be collectively represented as a compound of the formula:

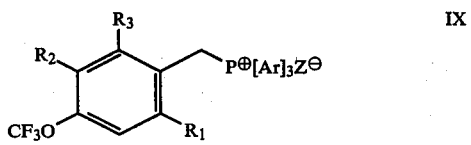

IX wherein $R_1$-$R_3$, Ar are as above and Z is halo or an anion of an organic acid.

The phosphonium salts of formula VI or VIII (i.e., compound IX) can be reacted with a compound of formula X via a Wittig procedure to form the inventive compounds of formula Ia which correspond to compounds of formula I wherein $R_4$ is

and $R_5$ is lower alkoxy.

In accordance with the above Wittig procedure, compound IX and X are reacted in the presence of any inorganic or organic acid binding agent. Typical acid binding agents include alkyllithium (e.g., n-butyllithium and methyllithium), alkali metal hydroxides and alcoholates (e.g., sodium hydroxide and sodium methylate), tertiary amines (e.g., triethylamine and pyridine) and alkaline oxides which may be alkyl substituted (e.g., ethylene oxide and 1,2-butylene oxide). Although not necessary, the reaction can proceed in an inert solvent such as diethyl ether and tetrahydrofuran or in an aliphatic or aromatic hydrocarbon such as hexane, benzene or toluene. The temperature of the reaction is not critical but the reaction generally proceeds between about −50° C. and about +60° C. A temperature of between about −45° C. and about −25° C. is preferred.

According to the present invention, conventional procedures may be applied to compound Ia to produce compounds of formula I wherein $R_4$ is —CH$_2$OH,

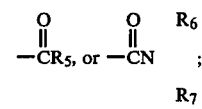

$R_5$ is hydrogen or hydroxy and $R_6$ and $R_7$ each are hydrogen or lower alkyl.

Typical processes contemplated by the present invention include: reducing a carboxylic acid ester of formula Ia which was obtained according to the above procedures to its corresponding alcohol of formula Ib ($R_4$ is —CH$_2$OH); oxidizing the alcohol of formula Ib to its corresponding aldehyde of formula Ic ($R_4$ is

and $R_5$ is hydrogen); hydrolyzing a carboxylic acid ester of formula Ia to its corresponding carboxylic acid of formula Id ($R_4$ is

and $R_5$ is hydroxy); and converting the carboxylic acid of formula Id to unsubstituted and lower alkyl substituted amides of formula Ie ($R_4$ is

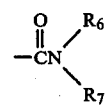

and $R_6$ and $R_7$ each are hydrogen or lower alkyl).

More particularly, compound Ia is converted to the alcohol of formula Ib by conventional reduction techniques. Any known method for reducing an ester to an alcohol can be utilized to carry out this conversion. A preferred reduction method includes reacting compound Ia with diisobutyl aluminumhydride in an ether solvent to produce alcohol Ib. Although temperature is not critical, the reaction generally proceeds between a temperature of about −70° C. to about 40° C. A temperature of about 0° C. is preferred.

Alcohol Ib can be oxidized to aldehyde Ic by any conventional technique for oxidizing an alcohol to an aldehyde. Illustratively, compound Ib can be treated with an oxidizing agent capable of converting an alcohol to an aldehyde. Activated magnesium dioxide is a suitable oxidizing agent.

Compound Ia can also be converted to the carboxylic acid of formula Id by basic or acidic hydrolysis. Any conventional method for hydrolyzing an ester to an acid may be employed. A typical method includes reacting compound Ia in an alkali metal or alkaline earth metal hydroxide (e.g., potassium hydroxide) in the presence of an aqueous alcohol (e.g., methanol or propanol). Reaction temperature is not critical and can vary from about 50° C. to about 100° C. A temperature of about 80° C. is preferred.

Compound Id can be converted to the unsubstituted amide or lower alkyl substituted amide of formula Ie via any conventional method of amidating a carboxylic acid. Preferably, compound Id is reacted with an appropriate unsubstituted or lower alkyl substituted amine (i.e., mono-(lower alkyl)carbamoyl or di-(lower alkyl)carbamoyl) in the presence of carbonyl diimidazole to produce a corresponding unsubstituted or lower alkyl substituted amide. Preferably, the reaction occurs in a polar organic solvent such as tetrahydrofuran or diethyl ether.

In Scheme I, the compounds and reactants for formulas II, VII and X are known or can be prepared from known compounds by conventional procedures.

In accordance with another aspect of the present invention, compound V can be converted to compound Ia via a phosphonate of the formula:

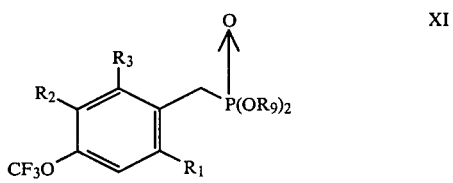

XI wherein $R_1$–$R_3$ are as above and $R_9$ is lower alkyl.

Illustratively, compound V is reacted with a tri(lower)alkyl phosphite (e.g., triethyl phosphite) by a conventional Michaelis-Arbuzov procedure to form the corresponding phosphonate of formula XI. Although temperature is not critical, the reaction generally proceeds between about 35° C. and 150° C., about 100° C. is preferred.

The phosphonate of formula XI then is reacted with the compound of formula X by a conventional Horner procedure. This procedure generally occurs with the aid of a base such as an alkali metal or alkaline earth metal hydroxide (e.g., sodium hydroxide) or an alkali metal alcoholate (e.g., sodium methylate). Preferably, the procedure is carried out in the presence of an inert organic solvent such as benzene, toluene, dimethylformamide, tetrahydrofuran and the like. Although temperature is not critical, the Horner procedure generally is carried out between about 20° C. and about 110° C., about 60° C. is preferred.

The compounds of formula I can occur as a cis-trans mixture which can be separated in a known manner into the corresponding cis and trans components or isomerized in a known manner to the all-trans compounds.

Any conventional method of double bond isomerization can be utilized to form the all-trans compound. For example, an 8-cis/trans mixture of compound I can be treated with catalytic amounts of iodine in an organic solvent (e.g., benzene and toluene) to produce the desired all-trans product. Although temperature is not critical, the isomerization generally occurs between about 10° C. to about 60° C. The preferred temperature values are from about 25° C. to about 35° C.

The compounds of formula I are pharmacodynamically valuable. They are effective in regressing the growth of tumors such as papillomas as well as in regressing the growth of chondrosarcoma.

The compounds of formula I are also useful as medicaments for the topical and systemic therapy of acne, psoriasis and other related dermatological disorders which are characterized by an increased or pathologically altered cornification, as well as inflammatory and allergic dermatological conditions. They also can be used to treat disorders which are characterized by inflammatory or degenerative alterations of the mucous membranes.

To examine their pharmacodynamic properties, the compounds of the present invention were subjected to skin papilloma tests generally as described by W. Bollag in *Experentia*, Vol. 27 (1971) pp. 90 et seq. and to hypervitaminosis-A dosage experiments generally as defined by W. Bollag in *Europ. J. Cancer*, Vol. 10 (1974) pp. 731–737. The procedure is described further herebelow under Methodology and the results of these experiments are illustrated in Table 2.

Methodology

Papillomas were induced by painting 7,12-dimethylbenz[α]anthracene and croton oil on the backs of Swiss albino mice. After 3–8 months, multiple papillomas developed on the mice.

The experiment was carried out over a 2 week period with groups of 4 mice. The sum of the diameters of the papillomas in each mouse and the average values for each group of 4 mice treated with the compounds listed in Table 2 were calculated. These measurements were made on day zero and on day 14 (2 weeks after the first medication was given).

The mice received a suspension of the preparation intraperitoneally and were dosed on day 1 and day 8 of the test period. The papilloma diameters were measured on day zero and day 14 of the experiment. The increase or decrease of the average diameter of the papillomas for a given dose (total application on day 1 and 8) was calculated and recorded in percent of the starting value on day zero. A decrease in the average diameter of the papillomas was noted as a negative value.

The vitamin A hypervitaminosis test was carried out on the mice weighing 25–27 g. which over a 14 day period receive 10 i.p. injections of the test substance suspended in arachis oil. In following Table 1, the symptoms were evaluated using a scale from 0 to 4.

TABLE 1

| Grade | 0 | 1 | 2 | 3 | 4 |
|---|---|---|---|---|---|
| Loss of Weight | 1 g. | 1–3 g. | 4–6 g. | 7–9 g. | 10 g. |
| Skin desquamation | none | slight | moderate | severe | very severe |
| Loss of hair | none | slight | moderate | severe | very severe |
| Bone fractures of extremities (numbers, macroscopic observation) | 0 | 1 | 2 | 3 | 4 |

Hypervitaminosis-A was defined as that condition of the mice wherein the addition of all the symptom grades yields at least a value of 3. The lowest daily dose able to cause hypervitaminosis-A in the 14 day study was recorded.

From the data resulting from the above experiments, a therapeutic index was calculated. For this purpose, the therapeutic index was defined as the quotient of the lowest daily dose causing vitamin A hypervitaminosis (numerator) and the lowest dose (total application) causing approximately 50% regression of papilloma diameters (denominator).

A high daily dose causing vitamin A hypervitaminosis indicated insubstantial toxicity. A low daily dose causing approximately 50% regression of papilloma indicated substantial activity. The quotient of a high dose causing hypervitaminosis-A advantageously and a low dose causing 50% papilloma reduction and resulted in a high therapeutic index. The higher the therapeutic index for a given compound, the more favorable the relation between the antineoplastic activity (regression of papillomas) and the toxicity (vitamin A hypervitaminosis) of the compound under concerns. Such a favorable relation is an indication that the compound is effective as an antitumor agent.

ceutically acceptable inert or pharmacodynamically active additives. For example, tablets or granules can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor improving additives and pharmaceutically acceptable substances commonly used as preservatives, stabilizers, moisture retainers or emulsifiers, salts for varying the osmotic pressure, buffers and

TABLE 2

| Compound | Hypervit. A (mg/kg/day) | Papilloma Dose (mg/kg/week) % Change | Therap. Index |
|---|---|---|---|
| | 1. series | | |
| | >400 | 400 − 56<br>200 − 53<br>100 − 29 | $\frac{>400}{200} = >2$ |
| | 2. series | | |
| CF$_3$O—Ar—CH=CH—...—COOC$_2$H$_5$ | 400 | 400 − 57<br>200 − 42<br>100 − 27<br>50 − 8 | $\frac{400}{200} = 2$ |
| CF$_3$O—Ar—CH=CH—...—COOH | 50 | 400 − 84<br>200 − 63<br>100 − 16<br>50 − 21<br>25 + 7 | $\frac{50}{150} = 0.3$ |
| CF$_3$O—Ar—CH=CH—...—CONHC$_2$H$_5$ | >400 | 400 − 41<br>200 − 24<br>100 − 18 | $\frac{>400}{>400} = \sim 1$ |
| CF$_3$O—Ar(Cl,Cl)—CH=CH—...—COOC$_2$H$_5$ | 200 | 100 − 57<br>50 − 50<br>25 − 12 | $\frac{200}{50} = 4$ |
| CF$_3$O—Ar—CH=CH—...—COOC$_2$H$_5$ | >400 | 400 − 14 | — |

The compounds of formula I can be used as medicaments in the form of pharmaceutical preparations. At least one of the compounds of formula I can be utilized in association with a compatible carrier material to form the pharmaceutical preparations.

Illustratively, pharmaceutical preparations for systemic administration can be prepared by adding a polyene compound of formula I as the active ingredient to pharmaceutically acceptable, non-toxic, inert solid or liquid carriers which are usually included in such preparations. The pharmaceutical preparations can be administered enterally, parenterally or topically. Suitable preparations for enteral administration are, for example, tablets, capsules, dragees, syrups, suspensions, solutions and suppositories. Suitable pharmaceutical preparations for parenteral administration are infusion solutions.

The dosages in which the compounds are administered can be varied according to the mode and route of administration and according to the requirements of the patient. For example, the compounds can be administered in amounts of from 0.5 mg. to 300 mg. daily in one or more dosages.

In addition to the active compounds of this invention, the pharmaceutical preparations can contain pharmaceutically acceptable additives can also be present in the pharmaceutical preparations.

The aforementioned pharmaceutically acceptable carrier materials and diluents are well known to the pharmaceutical compounding art and can be organic or inorganic substances such as water, gelatin, lactose, magnesium, stearate, talc, gum arabic, polyalkyleneglycols and the like. It is, of course, a prerequisite that all excipients used in the preparation of the pharmaceutical preparations are non-toxic and pharmaceutically acceptable.

For topical administration, the compounds of this invention are expediently prepared as salves, tinctures, creams, solutions, lotions, sprays, suspensions and the like. Ointments, creams and solutions are preferred. These pharmaceutical preparations for topical administration can be prepared by mixing a compound of this invention as the active ingredient with pharmaceutically acceptable non-toxic, inert, solid or liquid carriers which are customary in such preparations and which are suitable for topical administration.

Conventional pharmaceutically acceptable antioxidants (e.g., tocopherol, N-methyl-alpha-tocopheramine butylated hydroxyanisole and butylated hydroxytoluene) can also be incorporated into the pharmaceutical preparations containing the polyene compounds of this invention.

The following Examples illustrate the present invention. Examples 1-11 were carried out as written. In the Examples, the ether is diethyl ether and temperatures are expressed in degrees Celsius (°C.) unless otherwise specified. Room temperature is about 23° C. THF is tetrahydrofuran. In the Examples, "work up in the usual manner" connotes that the following procedure was performed: The reaction mixture was partitioned between water and an organic solvent (e.g., diethyl ether, methylene chloride). The organic extracts were combined, washed with water or brine, dried with magnesium sulfate or sodium sulfate, filtered and evaporated under reduced pressure on a rotary evaporator.

EXAMPLE 1

Carbonochloridothioic Acid 0-2,3,5-Trimethylphenyl Ester 2,3,5-Trimethylphenol (201 g, 1.48 mol) was dissolved in a solution of 1 liter of water containing 59.2 g (1.48 mol) of sodium hydroxide, with heating as necessary to obtain a solution, and filtered. Thiophosgene (170 g, 1.48 mol; 85% in CCl4) in 900 ml of chloroform in a 3-liter flask equipped with a mechanical stirrer, thermometer, and 2-liter addition funnel was cooled to −10° C. with an ice-acetone bath. To this cooled, vigorously stirred thiophosgene solution, the phenoxide solution was added over a 2-hour period at a rate such that the internal temperature remained below 0° C. After the addition was complete, the reaction was stirred for an additional 15 minutes. The dark solution was poured into 1.5 liters of hexane and 1 liter of saturated sodium chloride solution, both of which had been precooled to 5° C. The organic layer was separated, dried (MgSO4), filtered, and concentrated under reduced pressure to give a crude oily product, which was distilled at 90°-95° C./0.3 mm to give 287 g of carbonochloridothioic acid 0-2,3,5-trimethylphenyl ester.

EXAMPLE 2

2,3,5-Trimethyl-1-trifluoromethoxybenzene

Carbonochloridothioic acid 0-2,3,5-trimethylphenyl ester (100 g, 0.47 mol) in 1000 ml of methylene chloride in a 2-liter, 3-necked, round-bottomed flask equipped with an internal low-temperature thermometer and under an atmosphere of argon was cooled to −35° C. in a dry ice-acetone bath but not allowed to freeze. A solution of 20.0 ml (0.25 mol; 2.6 g/ml) of molybdenum hexafluoride (Ventron) in 40 ml of methylene chloride was added at a rate such that the temperature did not rise above −25° C. After the addition was complete, the black mixture was allowed to warm to room temperature. The internal thermometer and addition funnel were replaced with glass stoppers and a distillation head was attached. Most of the methylene chloride was distilled off leaving a black residue. The oil bath temperature was raised to 100° C. over 0.5 hour and maintained for 15 minutes. The condenser and receiver containing some methylene chloride were removed and replaced with a 250-ml, round-bottomed flask cooled in a dry ice-acetone bath. The product was distilled at 140° C. (oil bath temperature) and water aspirator pressure. The bath temperature was raised to 180° C. and a heat gun was used to remove all of the product from the flask and distillation head. The product was diluted with 100 ml of hexane; the hexane solution was washed once with 50 ml of 5% sodium bicarbonate solution. The organic layer was dried (MgSO4), filtered, concentrated, and distilled to give 22 g of 2,3,5-trimethyl-1-trifluoromethoxybenzene: bp 76°-77° C.

The solution of molybdenum hexafluoride of this Example 2 was prepared as follows: A dropping funnel with pressure equalizing side arm was placed in a 2-necked, round-bottomed flask. Argon was introduced through one neck of the flask and allowed to sweep through the funnel. The methylene chloride was added to the funnel, and the required amount of molybdenum hexafluoride was added directly from the cylinder.

EXAMPLE 3

(4-Trifluoromethoxy-2,3,6-trimethylphenyl)methyltriphenylphosphonium Chloride

A solution of 31.5 (0.15 mol) of 2,3,5-trimethyl-1-trifluoromethoxybenzene, 315 ml of acetic acid, 31.5 ml of concentrated hydrochloric acid, 31.5 ml of aqueous formaldehyde and 13 g (0.185 mol) of chloromethyl methyl ether was heated to 85° C. for 72 hours. (Small samples were worked up periodically after 48 hours to optimize the ratio of monochloromethyl product:dichloromethyl product:starting material). The solution was then cooled, poured into 1.5 liters of water and extracted with 3×500 ml of hexane. The hexane extracts were washed with 1 liter of water and 500 ml of saturated NaHCO3 solution, dried (MgSO4), filtered, and concentrated to give 30 g of crude (4-trifluoromethoxy 2,3,6-trimethylphenyl)methyl chloride containing some starting material, 2,3,5-trimethyl-1-trifluoromethoxybenzene, which was removed by distillation at 24°-30° C./0.05 mm. The residue (22 g), crude (4-trifluoromethoxy-2,3,6-trimethylphenyl)methyl chloride, was used directly in the next step.

The crude (4-trifluoromethoxy-2,3,6-trimethylphenyl)methyl chloride, 27.5 g (0.104 mol) of triphenylphosphine and 250 ml of acetonitrile were heated to reflux for 20 hours. The solvent was removed on a rotary evaporator at room temperature and the residue was triturated with 300 ml of ethyl acetate. The resulting solid was filtered, dissolved in 250 ml of hot acetonitrile and treated with 1 liter of ethyl acetate. The mixture was allowed to stand 2 hours; 38 g of (4-trifluoromethoxy-2,3,6-trimethylphenyl)methyltriphenylphosphonium chloride was collected; mp 272°-274° C. In a similar manner, the mother liquor afforded an additional 10.5 g of product.

EXAMPLE 4

Ethyl-(2E,4E,6E,8E)-3,7-Dimethyl-9-[2,3,6-trimethyl-4-(trifluoromethoxy)phenyl]-nonatetraenoate A suspension of 12.2 g (24 mmol) of (4-trifluoromethoxy-2,3,6-trimethylphenyl)methyltriphenylphosphonium chloride in 490 ml of dry THF was cooled to 45° C. and treated rapidly (over ~5 minutes) with 11.1 ml (25.5 mmol) of n-butyl lithium (2.3M in hexane) at −35° to −45° C. The reaction mixture was maintained at that temperature for 15 minutes, allowed to warm slowly to −25° C. at which time it became a slightly turbid orange solution. The mixture was cooled to −45° to −50° C. and 7.0 g (33 mmol) of ethyl-(2E,4E,6E)-3,7-dimethyl-8-oxo-octatrienoate in 50 ml of dry THF was added rapidly. The orange color disappeared; the reaction mixture was stirred at −25° C. for 2 hours, then allowed to warm to 0° C. over 1 hour and maintained at that temperature for 2 hours. The mixture was then poured into 1 liter of cold water and extracted with 250-ml portions of hexane. The organic phase was combined, washed successively with 500 ml of cold water, 2×500 ml of a 60% by volume methanol-water solution, and 500 ml of saturated NaCl solution, dried (MgSO₄), filtered and concentrated. The resulting yellow oil was purified by HPLC (2 silica gel columns, 2% ethyl acetate in hexane as elutant) to give 5.79 g of ethyl-(2E,4E,6E,8E)-3,7-dimethyl-9-[2,3,6-trimethyl-4-(trifluoromethoxy)phenyl]-nonatetraenoate; mp 47°–49° C.

The 8(Z)-isomer ethyl-(2E,4E,6E,8Z)-3,7-dimethyl-9-[2,3,6-trimethyl-4-(trifluoromethoxy)phenyl]-nonatetraenoate (1.25 g, 12.8%) was also obtained from the HPLC purification above.

The 8Z-isomer ethyl-(2E,4E,6E,8Z)-3,7-dimethyl-9-[2,3,6-trimethyl-4-(trifluoromethoxy)phenyl]-nonatetraenoate was readily converted to ethyl-(2E,4E,6E,8E)-3,7-dimethyl-9-[2,3,6-trimethyl-4-(trifluoromethoxy)phenyl]-nonatetraenoate and the 2(Z)-isomer ethyl-(2Z,4E,6E,8E)-3,7-dimethyl-9-[2,3,6-trimethyl-4-(trifluoromethoxy)-phenyl]-nonatetraenoate by treatment with iodine in chloroform solution. HPLC separation of this mixture afforded additional ethyl-(2E,4E,6E,8E)-3,7-dimethyl-9-[2,3,6-trimethyl-4-(trifluoromethoxy)phenyl]-nonatetraenoate and fractions enriched in the 2(Z)-isomer ethyl-(2Z,4E,6E,8E)-3,7-dimethyl-9-[2,3,6-trimethyl-4-(trifluoromethoxy)phenyl]-nonatetraenoate. Further HPLC purification of the latter fractions gave pure ethyl-(2Z,4E,6E,8E)-3,7-dimethyl-9-[2,3,6-trimethyl-4-(trifluoromethoxy)phenyl]-nonatetraenoate, which after recrystallization from pentane had a melting point of 59°–67° C.

EXAMPLE 5

(2E,4E,6E,8E)-3,7-Dimethyl-9-[2,3,6-trimethyl-4-(trifluoromethoxy)phenyl]-nonatetraenoic Acid A mixture of 15.3 g (0.0375 mol) of ethyl-(2E,4E,6E,8E)-3,7-dimethyl-9-[2,3,6-trimethyl-4-(trifluoromethoxy)phenyl]-nonatetraenoate, 76.5 ml of dioxane and 30 ml of 2N methanolic KOH was heated to reflux for 4 hours. The mixture was then poured into 300 ml of ice-H₂O and acidified to pH 2 with 2N sulfuric acid. The yellow precipitate was extracted with 3×200 ml of chloroform, washed with sodium chloride solution and dried (MgSO₄). Evaporation of the solvent gave a yellow solid, which was treated with 150 ml of hexane and filtered to give 12 g of crude (2E,4E,6E,8E)-3,7-dimethyl-9-[2,3,6-trimethyl-4-(trifluoromethoxy)phenyl]-nonatetraenoic acid. Recrystallization from 200 ml of ethyl acetate gave 9.25 g of (2E,4E,6E,8E,)-3,7-dimethyl-9-[2,3,6-trimethyl-4-(trifluoromethoxy)phenyl]-nonatetraenoic acid; mp 190°–193° C.

EXAMPLE 6

N-Ethyl(2E,4E,6E,8E)-3,7-dimethyl-9-[2,3,6-trimethyl-4-(trifluoromethoxy)phenyl]-nonatetraenamide A solution of 2.0 g (5.3 mmol) of (2E,4E,6E,8E)-3,7-dimethyl-9-[2,3,6-trimethyl-4-(trifluoromethoxy)phenyl]-nonatetraenoic acid in 60 ml of dry THF and 1.6 g of (10 mmol) of carbonyldiimidazole was heated to 35°–40° C. for 0.5 hour. The reaction mixture was cooled to −10° C. and excess gaseous ethyl amine was introduced. The resulting mixture was stirred for 1 hour at 23° C., diluted with 100 ml of hexane, and filtered through silica gel (200 g, 1:1 ethyl acetate-hexane as elutant). Further chromatographic purification (silicia gel, 5 to 10% ethyl acetate in methylene chloride) gave a yellow solid which, after recrystallization (ethyl acetate-hexane), yielded 1.4 g of N-ethyl(2E,4E,6E,8E)-3,7-dimethyl-9-[2,3,6-trimethyl-4-(trifluoromethoxy)phenyl]-nonatetraenamide; mp 198°–200° C.

EXAMPLE 7

Carbonochloridothioic acid 0-2,5-dichloro-3-methylphenyl ester

A solution of 65 g (0.38 mole) of 3,5-dichloro-o-cresol in 500 ml of 0.75M aqueous sodium hydroxide was cooled to 5° C. and added to a mechanically-stirred solution of 85 g (0.38 mol) of thiophosgene (85% by volume in CCl₄) in 400 ml of chloroform at 0° C. over a period of 0.5 hour. The mixture was stirred for an additional 0.5 hour and then poured into ice water. The chloroform layer was separated, washed with 500 ml. of cold 5% sodium hydroxide, and 500 ml of cold brine, dried (MgSO₄), and concentrated. The residue was distilled to give 73 g of carbonochloridothioic acid 0-2,5-dichloro-3-methylphenyl ester; bp 107°–111° C. (0.3 mm).

EXAMPLE 8

1,3-Dichloro-5-(trifluoromethoxy)-4-methylbenzene

To a solution of 35 g (0.14 mole) of carbonochloridothioic acid 0-2,5-dichloro-3-methylphenyl ester in 250 ml of methylene chloride at −35° C., a mixture of 4.1 ml (0.050 mole) of molybdenum hexafluoride in 20 ml of methylene chloride was added quickly. The reaction was allowed to warm slowly to 20° C. over a 1-hour period and heated as described above in Example 2 for the preparation of 2,3,5-trimethyl-1-trifluoromethoxybenzene. The distilled material was treated as described therein and redistilled to give 10.3 g of 1,3-dichloro-5-(trifluoromethoxy)-4-methylbenzene; bp 69°–71° C.

The solution of molybdenum hexafluoride of this Example 8 was prepared as follows: A dropping funnel with pressure equalizing side arm was placed in a 2-necked, round-bottomed flask. Argon was introduced through one neck of the flask and allowed to sweep through the funnel. The methylene chloride was added to the funnel, and the required amount of molybdenum hexafluoride was added directly from the cylinder.

EXAMPLE 9

1,3-Dichloro-2-chloromethyl-4-methyl-5-(trifluoromethoxy)benzene 1,3-Dichloro-5-(trifluoromethoxy)-4-methylbenzene (8.0 g, 33 mmol) and 5.0 g (78 mmol) of chloromethyl methyl ether were added to 50 ml of H₂SO₄ (98%) with stirring at 20° C. The temperature rose slowly to 30° C. The mixture was stirred for 15 hours, then poured into 200 ml of ice water and extracted with 2×100 ml portions of hexane. The hexane extracts were combined, washed with 100 ml of water, dried (MgSO₄), filtered, and concentrated. The residue was dissolved in 50 ml of hexane, filtered and concentrated. The resulting white solid was dried (25° C./0.001 mm) to give 9.0 g of 1,3-dichloro-2-chloromethyl-4-methyl-5-(trifluoromethoxy)benzene.

EXAMPLE 10

[[2,6-Dichloro-3-methyl-4-(trifluoromethoxy)phenyl]-methyl]triphenylphosphonium Chloride A solution of 8.0 g (27 mmol) of 1,3-dichloro-2-chloromethyl-4-methyl-5-(trifluoromethoxy)benzene in 250 ml of toluene was treated with 15.0 g (61 mmol) of triphenylphosphine and heated at 90° to 95° C. for 90 hours. During the heating period, the resulting solid product was removed periodically by filtration. The solid product was combined and dried (60° C./0.001 mm) to yield 12.0 g of phosphonium salt [[2,6-dichloro-3-methyl-4-(trifluoromethoxy)phenyl]methyl]triphenylphosphonium chloride.

EXAMPLE 11

(2E,4E,6E,8E)-3,7-Dimethyl-9-[2,6-dichloro-3-methyl-4-(trifluoromethoxy)phenyl]-nonatetraenoic Acid Ethyl Ester A solution of 5.1 g (8.8 mmol) of finely powdered phosphonium salt [[2,6-dichloro-3-methyl-4-(trifluoromethoxy)phenyl]-methyl]triphenylphosphonium chloride in 150 ml of dry THF was cooled to −70° C. and treated with 4.8 ml (11 mmol) of n-butyl lithium (2.3M in hexane). This mixture was stirred at −70° C. for 15 minutes and then treated with a solution of 4.0 g (19 mmol) of (2E,4E,6E,8E)-3,7-dimethyl-8-oxoocta-trienoate in 15 ml of THF. The mixture was allowed to warm slowly to 0° C., maintained at that temperature for 4 hours, then poured into 200 ml of water and extracted with 2×200 ml of hexane. The hexane extracts were combined and washed with 2×150 ml of a 60% MeOH/H$_2$O solution and 150 ml of saturated NaCl solution. The hexane layer was dried (MgSO$_4$), filtered and evaporated. Purification by HPLC (2 silica gel columns, 5% ethyl acetate in hexane) and crystallization from hexane gave 1.65 g by weight of (2E,4E,6E,8E)-3,7-dimethyl-9-[2,6-dichloro-3-methyl-4-(trifluoromethoxy)phenyl]-nonatetraenoic acid ethyl ester as light yellow crystals; mp 93°–94° C.

EXAMPLE 12

(2E,4E,6E,8E)-3,7-Dimethyl-9-[2,6-dichloro-3-methyl-4-(trifluoromethoxy)phenyl]-nonatetraenoic acid In a manner similar to that described in Example 5 for preparing (2E,4E,6E,8E)-3,7-dimethyl-9-[2,3,6-trimethyl-4-(trifluoromethoxy)phenyl]-nonatetraenoic acid, 0.04 mol of ethyl (2E,4E,6E,8E)-3,7-dimethyl-9-[2,6-dichloro-3-methyl-4-(trifluoromethoxy)phenyl]-nonatetraenoate in dioxane solution could be treated with 2N methanolic KOH at reflux for 4 hours. Acidification and extractive workup would produce (2E,4E,6E,8E)- 3,7-dimethyl-9-[2,6-dichloro-3-methyl-4-(trifluoromethyoxy)phenyl]-nonatetraenoic acid.

EXAMPLE 13

N-Ethyl (2E,4E,6E,8E)-3,7-dimethyl-9-[2,6-dichloro-3-methyl-4-(trifluoromethoxy)phenyl]-nonatetraenamide In a manner similar to that described in Example 6 for preparing N-ethyl (2E,4E,4E,8E)-3,7-dimethyl-9-[2,3,6-trimethyl-4-(trifluoromethoxy)phenyl]-nonatetraenamide, a solution of 5 mmol of (2E,4E,6E,8E)-3,7-dimethyl-9-[2,6-dichloro-3methyl-4-(trifluoromethoxy)phenyl]-nonatetraenoic acid in dry THF could be treated with 10 mmol of carbonyldiimidazole with heating to 35°–40° C. for 0.5 hour. The reaction mixture is cooled to −10° C. and excess gaseous ethyl amine is introduced.

After 1 hour, the desired N-ethyl (2E,4E,6E,8E)-3,7-dimethyl-9-[2,6-dichloro-3-methyl-4-(trifluoromethoxy)phenyl]-nonatetraenamide could be obtained by extractive workup and chromatographic purification in a conventional manner.

EXAMPLE 14

(2E,4E,6E,8E)-3,7-Dimethyl-9-[2,3,6-trimethyl-4-(trifluoromethoxy)phenyl]-nonatetraen-1-ol Ethyl (2E,4E,6E,8E)-3,7-dimethyl-9-[2,3,6-trimethyl-4-(trifluoromethoxy)phenyl]-nonatetraenoate could be dissolved in methylene chloride and treated with diisobutylaluminum hydride in hexane solution at −60° C. under argon. The temperature is raised to −10° C. for 10 to 30 minutes and then a saturated solution of magnesium sulfate is added. The mixture is stirred at 25° C. for 2 hours, filtered and evaporated to give (2E,4E,6E,8E)-3,7-dimethyl-9-[2,3,6-trimethyl-4-(trifluoromethoxy)phenyl]-nonatetraen-1-ol which is further purified by conventional chromatography.

EXAMPLE 15

(2E,4E,6E,8E)-3,7-Dimethyl-9-[2,3,6-trimethyl-4-(trifluoromethoxy)phenyl]-nonatetraen-1-al (2E,4E,6E,8E)-3,7-dimethyl-9-[2,3,6-trimethyl-4-(trifluoromethoxy)phenyl]-nonatetraen-1-ol (0.6 mmol) could be dissolved in 20 ml. of methylene chloride and added to a suspension of 1.1 g. of activated manganese dioxide in 40 ml. of methylene chloride. After filtration, the filtrate is concentrated to afford (2E,4E,6E,8E)-3,7-dimethyl-9-[2,3,6-trimethyl-4-(trifluoromethoxy)-phenyl]-nonatetraen-1-al which is purified by crystallization or chromatography in a conventional manner.

EXAMPLE 16

(2E,4E,6E,8E)-3,7-Dimethyl-9-[2,6-dichloro-3-methyl-4-(trifluoromethoxy)phenyl]-nonatetraen-1-ol In a manner similar to that described above for (2E,4E,6E,8E)-3,7-dimethyl-9-[2,3,6-trimethyl-4-(trifluoromethoxy)phenyl]-nonatetraen-1ol, (2E,4E,6E,8E)-3,7-dimethyl-9-[2,6-dichloro-3-methyl-4-(trifluoromethoxy)phenyl]-nonatetraenoic acid (31 mmol) in 100 ml. of methylene chloride is cooled to −60° C. under argon and treated with 69 mmol of diisobutylaluminium hydride.

After further reaction at −10° C., a saturated solution of magnesium sulfate is added. The mixture is stirred at 25° C. for 2 hours and filtered; the filtrate is concentrated to give the desired alcohol, which is further purified by crystallization or chromatography using conventional techniques.

EXAMPLE 17

(2E,4E,6E,8E)-3,7-Dimethyl-9-[2,6-dichloro-3-methyl-4-(trifluoromethoxy)phenyl]-nonatetraen-1-al (2E,4E,6E,8E)-3,7-dimethyl-9-[2,6-dichloro-3methyl-4-(trifluoromethoxy)phenyl]-nonatetraen-1-ol (0.6mmol) could be dissolved in 20 ml. of methylene chloride and added to a suspension of 1.1 g. of activated manganese dioxide in 40 ml. of methylene chloride with stirring. Ater the reaction is complete, the resulting mixture is filtered and the filtrate evaporated to give (2E,4E,6E,8E)-3,7-dimethyl-9-[2,6-dichloro-3-methyl-4-(trifluoromethoxy)phenyl]-nonatetraen-1-al, which is further purified by crystallization or chromatography using conventional procedures.

EXAMPLE 18

Capsule Formulation of ethyl (2E,4E,6E,8E)-3,7-dimethyl-9-[2,3,6-trimethyl-4-(trifluoromethoxy)phenyl]-nonatetraenoate

| | Mg./Capsule | | | | | |
|---|---|---|---|---|---|---|
| Compound | 0.5 | 5.0 | 25.0 | 50.0 | 100.0 | 300.0 |
| BHA | 0.01 | 0.02 | 0.05 | 0.1 | 0.1 | 0.1 |
| BHT | 0.01 | 0.02 | 0.05 | 0.1 | 0.1 | 0.1 |
| Fractionated Triglyceride of Coconut Oil | 130.0 | 130.0 | 200.0 | 250.0 | 500.0 | 900.0 |
| Wt. of Capsule- | 130.52 | 135.04 | 225.1 | 300.2 | 600.2 | 1200.2 |

1. Mix all ingredients together with warm fractionated triglyceride of Coconut Oil, in a suitable mixer. Mix well.
2. Encapsulate in a soft shell capsule of appropriate size.

EXAMPLE 19

Capsule Formulation of ethyl(2E,4E,6E,8E)-3,7-dimethyl-9-(2,3,6-trimethyl-4-trifluoromethoxy phenyl)nonatetraenoate

| | Mg./Capsule | | | | | |
|---|---|---|---|---|---|---|
| Compound | 0.5 | 5.0 | 25.0 | 50.0 | 100.0 | 300.0 |
| BHA | 0.01 | 0.02 | 0.05 | 0.1 | 0.1 | 0.1 |
| BHT | 0.01 | 0.02 | 0.05 | 0.1 | 0.1 | 0.1 |
| Fractionated Triglyceride of Coconut Oil | 130.0 | 130.0 | 200.0 | 250.0 | 500.0 | 900.0 |
| Wt. of Capsule- | 130.52 | 135.04 | 225.1 | 300.2 | 600.2 | 1200.2 |

1. Mix all ingredients together with warm fractionated triglyceride of Coconut Oil, in a suitable mixer. Mix well.
2. Encapsulate in a soft shell capsule of appropriate size.

EXAMPLE 20

Capsule Formulation for (2E,4E,6E,8E)-3,7-dimethyl-9-[2,3,6-trimethyl-4-(trifluoromethoxy)phenyl]nonatetraenoic acid

| | Mg./Capsule | | | | | |
|---|---|---|---|---|---|---|
| Compound | 0.5 | 5.0 | 25.0 | 50.0 | 100.0 | 300.0 |
| BHA | 0.01 | 0.02 | 0.05 | 0.1 | 0.1 | 0.1 |
| BHT | 0.01 | 0.02 | 0.05 | 0.1 | 0.1 | 0.1 |
| Fractionated Triglyceride of Coconut Oil | 130.0 | 130.0 | 200.0 | 250.0 | 500.0 | 900.0 |
| Wt. of Capsule- | 130.52 | 135.04 | 225.1 | 300.2 | 600.2 | 1200.2 |

1. Mix all ingredients together with warm fractionated triglyceride of Coconut Oil, in a suitable mixer. Mix well.
2. Encapsulate in a soft shell capsule of appropriate size.

EXAMPLE 21

Capsule Formulation for (2E,4E,6E,8E)-3,7l-dimethyl-9-[2,6-dichloro-3-methyl-4-(trifluoromethoxy)phenyl]-2,4,6,8-nonatetraenoic acid ethyl ester

| | Mg./Capsule | | | | | |
|---|---|---|---|---|---|---|
| Compound | 0.5 | 5.0 | 25.0 | 50.0 | 100.0 | 300.0 |
| BHA | 0.01 | 0.02 | 0.05 | 0.1 | 0.1 | 0.1 |
| BHT | 0.01 | 0.02 | 0.05 | 0.1 | 0.1 | 0.1 |
| Fractionated Triglyceride of Coconut Oil | 130.0 | 130.0 | 200.0 | 250.0 | 500.0 | 900.0 |
| Wt. of Capsule- | 130.52 | 135.04 | 225.1 | 300.2 | 600.2 | 1200.2 |

1. Mix all ingredients together with warm fractionated triglyceride of Coconut Oil, in a suitable mixer. Mix well.
2. Encapsulate in a soft shell capsule of appropriate size.

EXAMPLE 22

Capsule Formulation for N-ethyl(2E,4E,6E,8E)-3,7-dimethyl-9-[2,3,6-trimethyl-4-(trifluoromethoxy)phenyl]-nonatetraenamide

| | Mg./Capsule | | | | | |
|---|---|---|---|---|---|---|
| Compound | 0.5 | 5.0 | 25.0 | 50.0 | 100.0 | 300.0 |
| BHA | 0.01 | 0.02 | 0.05 | 0.1 | 0.1 | 0.1 |
| BHT | 0.01 | 0.02 | 0.05 | 0.1 | 0.1 | 0.1 |
| Fractionated Triglyceride of Coconut Oil | 130.0 | 130.0 | 200.0 | 250.0 | 500.0 | 900.0 |
| Wt. of Capsule- | 130.52 | 135.04 | 225.1 | 300.2 | 600.2 | 1200.2 |

1. Mix all ingredients together with warm fractionated triglyceride of Coconut Oil, in a suitable mixer. Mix well.
2. Encapsulate in a soft shell capsule of appropriate size.

I claim:

1. A compound of the formula:

$$\text{CF}_3\text{O}-\text{C}_6\text{H}(\text{R}_1)(\text{R}_2)(\text{R}_3)-\text{CH}=\text{C}(\text{CH}_3)-\text{CH}=\text{CH}-\text{C}(\text{CH}_3)=\text{CH}-\text{R}_4 \quad \text{I}$$

wherein $R_1$ is lower alkyl or halo; $R_2$ is lower alkyl;

$$-\overset{O}{\underset{\parallel}{C}}R_5, \text{ or } -\overset{O}{\underset{\parallel}{C}}N\overset{R_6}{\underset{R_7}{\diagdown}} \; ;$$

$R_5$ is hydrogen, hydroxy or lower alkoxy and $R_6$ and $R_7$ each are hydrogen or lower alkyl, in any of its various cis and trans stereoisomeric forms and mixtures thereof, or pharmaceutically acceptable salts thereof.

2. The compound of claim 1 wherein the compound is all trans.

3. The compound of claim 2 wherein $R_4$ is $-CH_2OH$.

4. The compound of claim 2 wherein $R_4$ is $$-\overset{O}{\underset{\parallel}{C}}R_5.$$

5. The compound of claim 4 wherein $R_5$ is hydrogen.

6. The compound of claim 4 wherein $R_5$ is hydroxy.

7. The compound of claim 6 wherein at least one of $R_1$ and $R_3$ is lower alkyl.

8. The compound of claim 7, (2E,4E,6E,8E)-3,7-dimethyl-9-[2,3,6-trimethyl-4-(trifluoromethoxy)phenyl]nonatetraenoic acid.

9. The compound of claim 6 wherein at least one of $R_1$ and $R_3$ is halo.

10. The compound of claim 4 wherein $R_5$ is lower alkoxy.

11. The compound of claim 10 wherein at least one of $R_1$ and $R_3$ is lower alkyl.

12. The compound of claim 11, ethyl-(2E,4E,6E,8E)-3,7-dimethyl-9-[2,3,6-trimethyl-4-(trifluoromethoxy)-phenyl]nonatetraenoate.

13. The compound of claim 10 wherein at least one of $R_1$ and $R_3$ is halo.

14. The compound of claim 13, (2E,4E,6E,8E)-3,7-dimethyl-9-[2,6-dichloro-3-methyl-4-(trifluoromethoxy)phenyl]nonatetraenoic acid ethyl ester.

15. The compound of claim 2 wherein $R_4$ is

and $R_6$ and $R_7$ each are hydrogen or lower alkyl.

16. The compound of claim 15 wherein $R_6$ and $R_7$ are hydrogen.

17. The compound of claim 15 wherein at least one of $R_1$ and $R_3$ is lower alkyl.

18. The compound of claim 17, N-ethyl(2E,4E,6E,8E)-3,7-dimethyl-9-[2,3,6-trimethyl-4-(trifluoromethoxy)-phenyl]nonatetraenamide.

19. The compound of claim 15 wherein at least one of $R_1$ and $R_3$ is halo.

* * * * *